United States Patent
Tran et al.

(10) Patent No.: US 11,227,689 B2
(45) Date of Patent: Jan. 18, 2022

(54) SYSTEMS AND METHODS FOR VERIFYING MEDICAL DIAGNOSES

(71) Applicant: Ferrum Health, Inc., San Francisco, CA (US)

(72) Inventors: Pelu S Tran, San Francisco, CA (US); Kenneth Ko, Santa Clara, CA (US)

(73) Assignee: FERRUM HEALTH, INC, San Francisco, CA (US)

( * ) Notice: Subject to any disclaimer, the term of this patent is extended or adjusted under 35 U.S.C. 154(b) by 320 days.

(21) Appl. No.: 16/155,804

(22) Filed: Oct. 9, 2018

(65) Prior Publication Data

US 2020/0111570 A1   Apr. 9, 2020

(51) Int. Cl.
*G16H 50/20*   (2018.01)
*G06N 20/00*   (2019.01)

(52) U.S. Cl.
CPC ............ *G16H 50/20* (2018.01); *G06N 20/00* (2019.01)

(58) Field of Classification Search
CPC ........ G16H 50/20; G16H 50/70; G16N 20/00; G06N 20/00; G06N 20/20
USPC ........................................................ 705/2–3
See application file for complete search history.

(56) References Cited

U.S. PATENT DOCUMENTS

| | | | |
|---|---|---|---|
| 2008/0103849 | A1 | 5/2008 | Forman et al. |
| 2009/0281981 | A1* | 11/2009 | Chen ................ G06N 20/20 706/56 |
| 2016/0129282 | A1 | 5/2016 | Yin et al. |
| 2016/0350919 | A1* | 12/2016 | Steigauf ............ G06K 9/6263 |
| 2016/0364862 | A1* | 12/2016 | Reicher ............ G16H 50/50 |
| 2020/0111024 | A1 | 4/2020 | Bergen et al. |
| 2020/0111572 | A1 | 4/2020 | Bergen et al. |

OTHER PUBLICATIONS

International Search Report, Application No. PCT/US19/55065, dated Mar. 12, 2020, 8 pages.

* cited by examiner

*Primary Examiner* — Jonathan Durant
*Assistant Examiner* — Benjamin L. Hanks
(74) *Attorney, Agent, or Firm* — Fountainhead Law Group P.C.

(57) ABSTRACT

Embodiments of the present disclosure pertain to verifying medical diagnoses. In one embodiment, a first classification unit is configured to process manually generated medical input data. The first classifier generates one or more first probabilities corresponding to one or more medical diagnoses. A second classification unit is configured to process machine generated medical input data associated with the manually generated medical data. The second classifier generates one or more second probabilities corresponding to the one or more medical diagnoses. A verification unit is configured to verify the manually generated input data by combining the first and second probabilities.

21 Claims, 5 Drawing Sheets

SYSTEMS AND METHODS FOR VERIFYING MEDICAL DIAGNOSES

BACKGROUND

The present disclosure relates to medical diagnostics and in particular, to systems and methods for verifying medical diagnoses.

Accurate diagnosis of a health condition can be a life or death situation for a patient. Typically, tests are conducted by hospitals and the results are analyzed by doctors. The doctor's analysis it typically memorialized in a doctor's report, which is manually created by the doctor, assistants, and/or other medical professionals.

However, human error can occur, and diagnoses are not always correct. An incorrect diagnosis may have dramatic impact on the life of a patient. It would be advantageous to have a diagnosis system that worked together with doctors to help verify the doctor's medical analysis.

SUMMARY

Embodiments of the present disclosure pertain to verifying medical diagnoses. In one embodiment, a first classification unit is configured to process manually generated medical input data. The first classifier generates one or more first probabilities corresponding to one or more medical diagnoses. A second classification unit is configured to process machine generated medical input data associated with the manually generated medical data. The second classifier generates one or more second probabilities corresponding to the one or more medical diagnoses. A verification unit is configured to verify the manually generated input data by combining the first and second probabilities.

Various embodiments of the techniques described herein may be implemented on a non-transitory machine-readable medium storing a program executable by at least one processing unit of a computer, the program comprising sets of instructions for performing the process steps described herein.

Other embodiments may include a computer system comprising a processor and a non-transitory machine-readable medium storing a program executable by the processor, the program comprising sets of instructions for performing the process steps described herein.

The following detailed description and accompanying drawings provide a better understanding of the nature and advantages of the present disclosure.

DETAILED DESCRIPTION

In the following description, for purposes of explanation, numerous examples and specific details are set forth in order to provide a thorough understanding of the present disclosure. Such examples and details are not to be construed as unduly limiting the elements of the claims or the claimed subject matter as a whole. It will be evident to one skilled in the art, based on the language of the different claims, that the claimed subject matter may include some or all of the features in these examples, alone or in combination, and may further include modifications and equivalents of the features and techniques described herein.

Figure 1A:
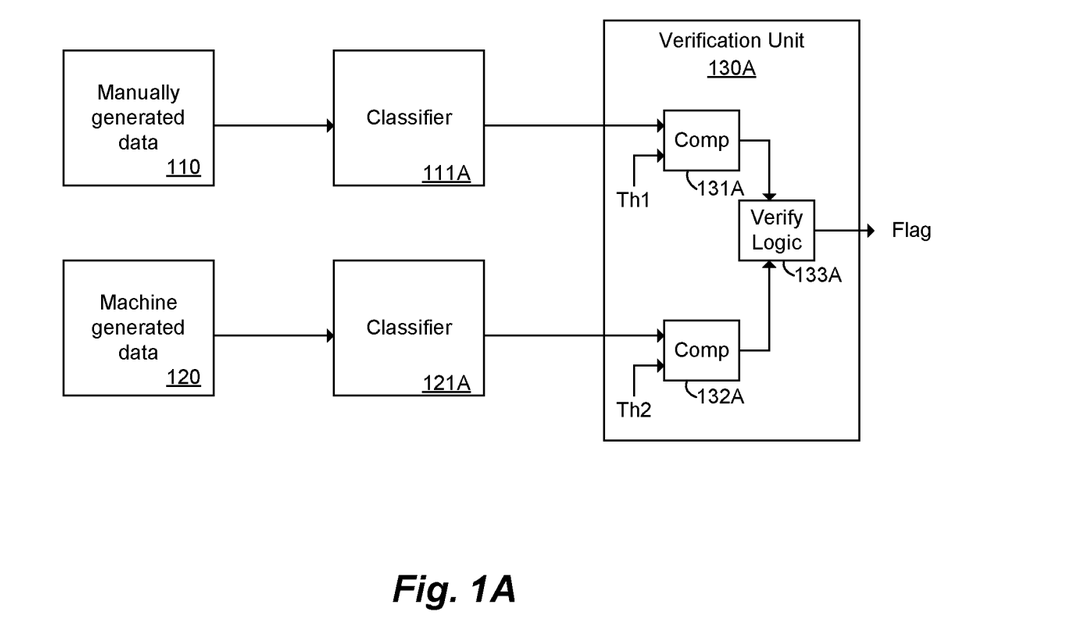
FIG. 1A illustrates a system for verifying medical diagnoses according to one embodiment.

FIG. 1A illustrates a system for verifying medical diagnoses according to one embodiment. Features and advantages of the present disclosure enable a computer system to verify medical diagnoses of a medical professional (e.g., a doctor), generated manually, with machine generated data, for example, which improves medical diagnostics capabilities of computer systems. For instance, a medical diagnosis verification system according to one embodiment may receive manually generated medical data 110 and machine generated medical data 120. Manually generated medical data 110 may include, for example, free-form text, text from one or more fields in an electronic form, or text corresponding to a selection in an electronic form. Such data may be created directly by a doctor (e.g., direct text entry) or using handwriting recognition software (for converting handwritten reports to text) or voice recognition software (for converting voice recorded reports to text), for example. Manually generated medical data 110 may be a doctor's report, radiologist's report, or any other medical professional's report, notes, or similar electronic health records (EHR) about a patient. Machine generated medical data 120 may include, for example, an electronic image, electronic test results, or a video, for example. Machine generated medical data 120 may include X-Rays, ultrasounds (US), magnetic resonance (MRI), Nuclear Medicine imaging, positron emission tomography (PET), computed tomography (CT scans), endoscopy (ES), mammograms (MG), digital radiography (DR), phosphor plate radiography, Histopathology, or ophthalmology to name just a few examples.

Typically, a health professional may indicate whether or not a particular patient has, or does not have, a particular diagnosis result. For example, a doctor may determine that a patient has a lung nodule by manually reviewing an image of the patient's lungs. However, if the doctor misses the lung nodule in the image, the patient is put at greater risk. Features and advantages of the present disclosure allow a computer system to analyze manually generated medical data (e.g., a doctor's report) and corresponding machine generated medical data (e.g., the image) to determine if the medical professional missed a diagnosis. For example, manually generated medical data 110 is processed by a first classification unit (or classifier) 111A, and the machine generated medical data 120 is processed by a second classification unit (or second classifier) 121A. In one embodiment, the classifiers 111A and 111B have been trained to detect one particular diagnosis (e.g., the existence or non-existence of a lung nodule). Classifier 111A receives the manually generated medical data 110 and processes the data to generate a first probability that the manually generated medical data 110 indicates a particular medical diagnosis (e.g., the existence or non-existence of a lung nodule).

Classifier 121A receives the machine generated medical data 120 and processes the data to generate a second probability that the machine generated medical data 120 indicates the same particular medical diagnosis (e.g., the existence or non-existence of a lung nodule). Manually generated data and machine generated data may be associated (e.g., a doctor's report and an associated image or test data) and related to the same patient, for example. Advantageously, each classifier 111A and 121A may be trained to recognize the same diagnoses so both classifiers output corresponding probabilities for the same patient based on different types of inputs. These probabilities may be input to a verification unit 130A configured to verify the manually generated input data by combining the first and second probabilities, for example. In the embodiment shown in FIG. 1A, the probability from classifier 111A is compared, at 131A, to a first threshold (Th1) to determine if the probability is high enough to result in a positive diagnosis. Similarly, the probability from classifier 111B is compared, at 132A, to a second threshold (Th2) to determine if the probability is high enough to result in a positive diagnosis. Outputs of the threshold comparisons at 131A and 132A are combined logically at 133A to verify the manually generated data 110. For example, if the probability from classifier 111A applied against threshold Th1 indicates a negative diagnosis (e.g., the non-existence of a lung nodule) and the probability from classifier 121A applied against threshold Th2 also indicates a negative diagnosis, then the manually generated data (e.g., the doctor's report) is verified. However, if the probability from classifier 111A applied against threshold Th1 indicates a negative diagnosis (e.g., no lung nodule detected) and the probability from classifier 121A applied against threshold Th2 also indicates a positive diagnosis (e.g., a lung nodule was detected by classifier 121A), then a potential error is detected. For example, in one embodiment, the verification unit 130A generates a verification flag when a probability based on the machine generated data indicates a positive result for a first diagnosis (e.g., there is a lung nodule), and a corresponding probability based on the manually generated data indicates a negative result for the first diagnosis (e.g., no lung nodule). Thus, a flag may be generated indicating that the manually generated data (e.g., the doctor's report) missed the diagnosis, and further remediation may be performed, for example.

Classifiers 111A and 121A may be medical classifiers configured for processing medical input data and generating probabilities corresponding to medical diagnoses. Classifiers 111A and 121A may be machine learning classifiers configured using training sets substantially similar in nature to the types of data inputs they are to receive and process, for example. Classifiers 111A and 121A may be implemented in computer code (instructions executable on a processor) that perform one of a variety of classification algorithms and configured using a training data set, for example.

Figure 1B:
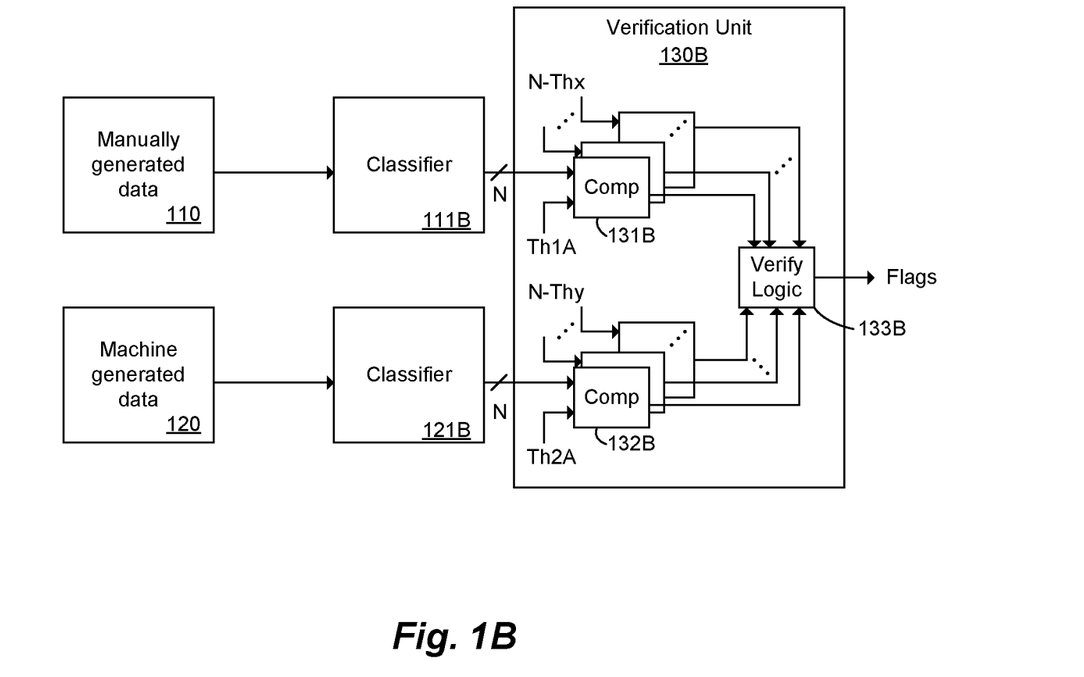
FIG. 1B illustrates a system for verifying medical diagnoses according to one embodiment.

FIG. 1B illustrates another embodiment of a medical diagnostic system according to an embodiment. In this embodiment, classifiers 111B and 121B are both configured to generate a plurality of probabilities corresponding to a plurality of different diagnoses. For example, classifier 111B may receive manually generated medical data 110 and produce probabilities for a lung nodule, a liver nodule, and a kidney nodule. Analogously, classifier 121B may receive machine generated medical data 120 and produce probabilities for a lung nodule, a liver nodule, and a kidney nodule. Each classifier 111B and 121B may produce N probabilities (where N is an integer), where each probability is a likelihood that a particular diagnosis is detected in the manually generated input data or machine generated input data, respectively. Each pair of corresponding probabilities for a particular diagnosis may be compared against a pair of thresholds ((th1A, th2A), (th1B, th2B), etc. . . . ), as illustrated here in verification unit 130B, for example. One threshold in each pair is applied to the probability from classifier 111B, and the other is applied to the probability from classifier 121B. In one embodiment described in more detail below, corresponding probabilities for a particular diagnosis from classifiers 111B and 121B (e.g., probabilities of a lung nodule based on manual and machine inputs) may be analyzed across a training set of data inputs (manually and machine generated) to generate the thresholds pairs.

The output of each pair of comparisons described above is processed by verification logic 133B, which in some embodiments may generate flags when a negative diagnosis is found in the manually generated data and a positive diagnosis is found for the machine generated data, for example. In one embodiment, different flags generated for different diagnoses may be sent to a user interface to inform a user that the manually generated data may have missed a diagnosis, for example.

Figure 2:
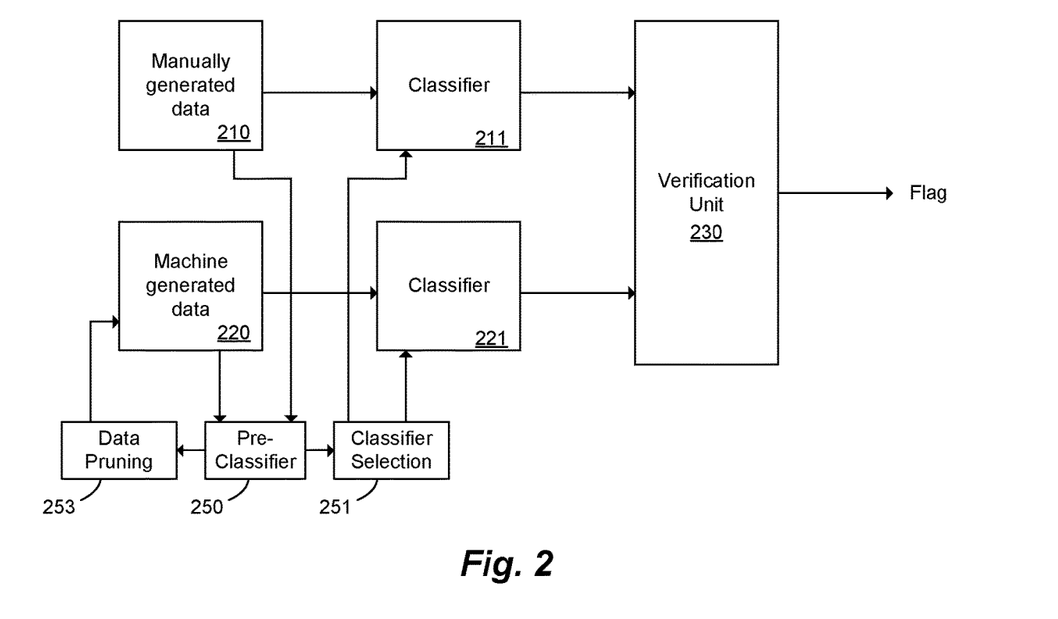
FIG. 2 illustrates a system for verifying medical diagnoses with pre-classification according to one embodiment.

FIG. 2 illustrates a system for verifying medical diagnoses with pre-classification according to one embodiment. Features and advantages of some embodiments of the disclosure include selecting customized classifiers for processing either or both of the manually generated data or machine generated data. For example, a pre-classification process 250 may receive either manually generated medical data 210 or machine generated medical data 220, or both. Further, based on the pre-classifying step, one of a plurality of classifiers may be selected at 251 for classifier 211 for processing the manually generated medical data or for classifier 212 for processing the machine generated medical data.

For example, in one embodiment, if the patient is determined during pre-classification to have a particular condition (e.g., a pre-existing condition), such as cancer, different classifiers may be used to obtain more accurate results in a more computationally efficient manner. For instance, pre-classifier 250 may be configured to receive manually generated data 210, such as a doctor's report, and determine if the report indicates the patient has or does not have cancer. If a patient is pre-classified as having cancer, a special classifier may be used for classifier 211 that is configured to understand manually generated cancer related terminology (e.g., a cancer specific language classifier), and another special classifier may be used for classifier 221 that has been trained to perform cancer specific diagnoses on cancer patients, for example. Accordingly, the system may determine, from the manually generated medical input data, whether or not a first medical condition is present. Next, first condition specific classifiers may be selected for classifier 211 and classifier 221 when the condition is present (e.g., when the patient has cancer), and second condition specific classifiers may be selected for classifier 211 and classifier 221 when the condition is not present (e.g., patient does not have cancer).

As another example, machine generated data 220 may be processed by a pre-classifier 250 to determine if an image, for example, shows a lung or an abdomen or other body part. Depending on the pre-classification result (e.g., which body part is in the image), a different classifier 221 may be selected. For example, if the body part is a lung, a classifier 221 may be selected that is trained to analyze lungs for lung nodules, and if the body part is an abdomen, a classifier 221 may be selected that is trained to analyze an abdomen for a pancreas nodule, for example.

As yet another example, an electronic health record or image (or both) may be pre-classified to determine if a patient has a metal prosthesis, for example. Accordingly, a different classifier 221 may be used to process machine generated medical data if the patient has a metal prosthesis versus if the patient does not have a metal prosthesis, for example.

As yet another example, a characteristic of a patient may be determined from the manually generated input data and used to select different classifiers for classifier 211 and 221. For example, if the manually generated medical data is analyzed and the patient's gender is determined, different classifiers may be selected for classifiers 211 and 221 based on whether the patient is male or female, for example, to optimize diagnostic analysis. In another embodiment, a patient's age may be used to select different classifiers for classifier 221 to improve diagnostic performance, for example.

As yet another example, the machine generated input data may have associated metadata that indicates a scan type. For example, a scan may be a CT scan, X-Ray, or MRI, for example, which may require different classifiers. Accordingly, pre-classification may comprise determining a scan type from the metadata and selecting classifier 221 based on the scan type specified in the metadata. Further, in one embodiment, classifier 211 may also be selected from a plurality of classifiers based on the scan type specified in the metadata. For example, doctors may have particular ways of writing about X-Ray scans that are different than the way they write about CT scans or MM scans. Performance of the system and quality of the results may be enhanced further by selecting particular classifiers 211 trained to process particular manually generated inputs for particular scan types, for example.

The above examples illustrate that, in some embodiments, pre-classification may act as a supervisory layer that analyzes the manually generated data or machine generated data, or both, and coordinates the selection of classifiers 211 and 221 to optimize recognition of diagnoses, for example. Accordingly, pre-classifier 250 may comprise one or more machine learning based classifiers for performing different classification tasks (receiving text or images and determining different aspects of each, such as body part), and pre-classifier 250 may also include logic based classifiers for selecting classifiers 211 and 221 based on various parameters, such as metadata associated with machine generated data or fields in a fillable form, for example. Advantageously, pre-classifying and selecting more precise classifiers for the manually generated data and associated machine generated data produces more precise results and reduces false positives and noise in the system, thereby improving the quality of the combined system, for example.

Figure 3:
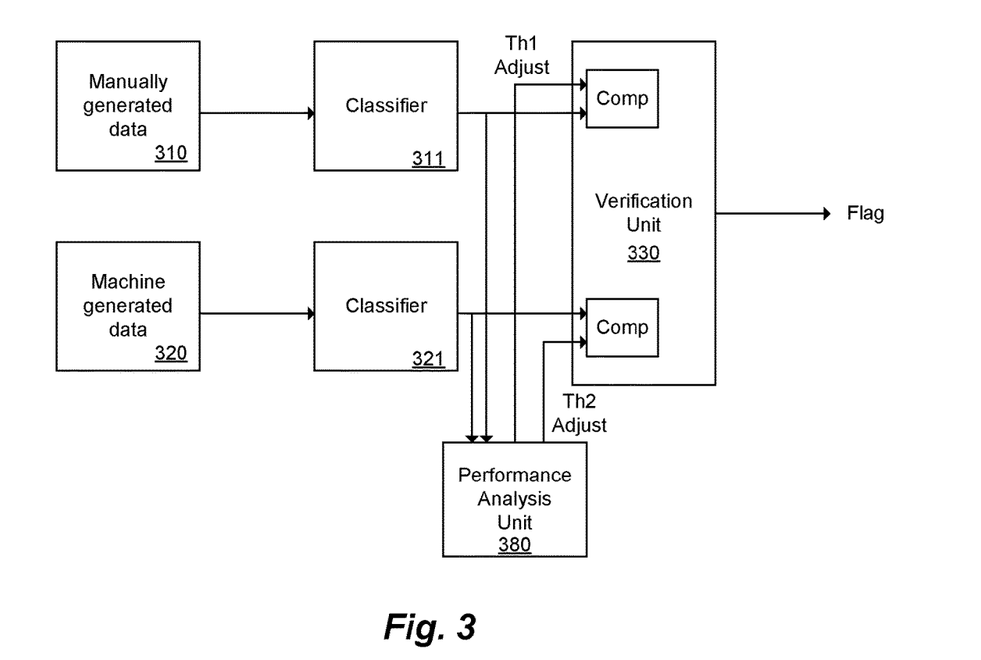
FIG. 3 illustrates a system for verifying medical diagnoses with threshold adjusting according to one embodiment.

FIG. 3 illustrates a system for verifying medical diagnoses with threshold adjusting according to one embodiment. As illustrated above, a wide range of classifiers may be selected and used to process manually generated and machine generated medical data. One aspect of the present disclosure includes determining optimum thresholds to be used to verify a diagnosis. For example, in one embodiment, training data of manually generated medical data inputs and associated machine generated medical inputs are used to determine optimum thresholds for comparison with the probabilities generated by classifiers 311 and 321. For instance, FIG. 3 may include a performance analysis unit 380. Performance analysis may include determining, based on a training data set, one or more first thresholds configured to determine if one or more probabilities from classifier 311 result in a positive result for a corresponding one or more diagnoses. Additionally, performance analysis may include determining, based on the training data set, one or more second thresholds configured to determine if one or more probabilities from classifier 321 result in a positive result for the corresponding one or more diagnoses. For the simple case of classifiers 311 and 321 each generating one probability corresponding to one diagnosis (e.g., lung nodules), performance analysis 380 may comprise processing training data for numerous reports and associated images in classifiers 311 and 312 to obtain probabilities relating to the diagnosis (e.g., relating to lung nodules). The training data results may be used to set Th1 and Th2 to obtain improved overall system performance. In one embodiment, false positive rates (a correct diagnosis based on manual data, but an incorrect diagnosis based on machine data), true positive rates (incorrect diagnosis based on manual data, but correct diagnosis based on machine data), and receiver operating characteristic (ROC) curves may be applied to determine optimum thresholds Th1 and Th2 to improve the accuracy of the combined classifiers 311 and 321, for example.

It is to be understood that the classification units, verification units, pre-classifiers, performance analysis units, comparison units, and other components described herein may be implemented as software components implemented as program code and instructions executable on one or more computer processors, for example.

Figure 4:
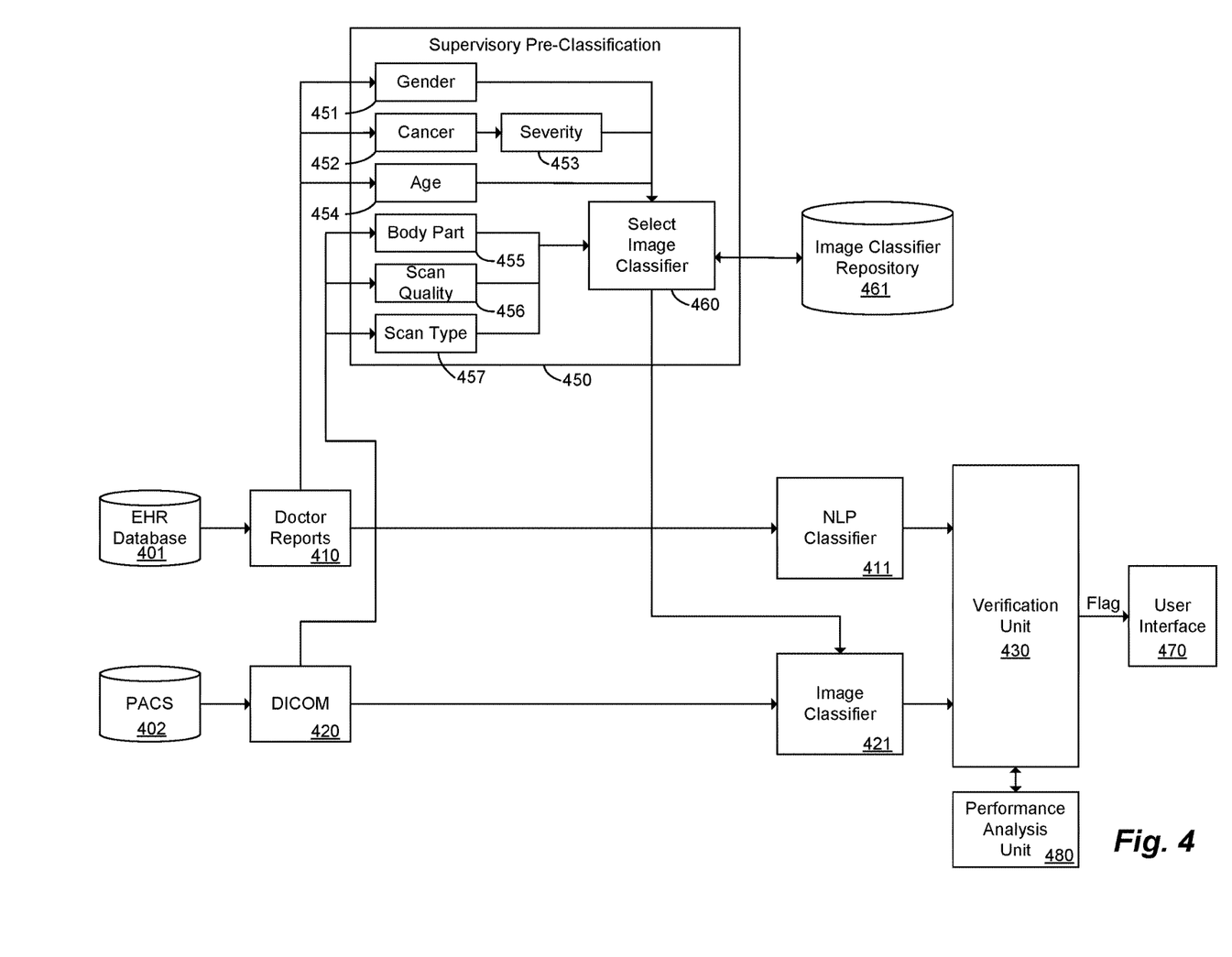
FIG. 4 illustrates an example system for verifying medical diagnoses according to another embodiment.

FIG. 4 illustrates an example system for verifying medical diagnoses according to another embodiment. In this example, manually generated medical data comprises electronic health records (EHR) stored in one or more EHR databases 401, and machine generated medical data comprises picture archiving and communication system (PACS) 402 for storing and accessing medical electronic images, for example. DICOM (Digital Imaging and Communications in Medicine) is a standard for storing and transmitting medical images. In this example, doctor's reports 410 for a patient and associated DICOMs (images) 420 for the patient are extracted from EHR database 401 and PACS 402, respectively. Reports 410 and DICOMs 420 may be sent to supervisory pre-classifier 450 for processing to determine an appropriate classifier to achieve optimum overall system results, for example. For example, doctor's reports 410 may be analyzed for gender 451, pre-existing cancer 452 and severity 453, and/or age 454, for example. Accordingly, gender, age, and the existence/non-existence of cancer, and its severity, may be used to select an image classifier at 460, for example. Similarly, electronic images (DICOMs) 420 may be pre-classified for a body part 455, scan quality 456, and/or scan type 457, for example, and the results used to select an image classifier 460. In this example, different classifier models may be stored in an image classifier repository, and an optimum classifier 421 may be selected and used for classification of the DICOMs 420. Similarly, pre-classification processes may be used for selecting an natural language processing (NLP) classifier 411 in other embodiments, and the example shown here is merely illustrative.

Doctor's reports, in some embodiments, may be free form text. In this example, such reports 410 are processed by a natural language processor (NLP) classifier 411 trained to classify manually generated reports into one or more particular diagnoses (e.g., lung nodule—yes/no). Accordingly, NLP classifier 411 outputs one or more probabilities, where each probability corresponds to one diagnosis that classifier 411 is trained to analyze. Each probability is a number representing the probability that a particular diagnosis exists based on the input report 410, for example. Similarly, a DICOM 420 for the same patient, which is associated with the doctor's report processed by NLP classifier 411, may be processed by an image classifier 421. Image classifier 421 likewise outputs one or more probabilities, where each probability corresponds to one diagnosis classifier 421 is trained to recognize. Advantageously, each classifier 411 and 421 is trained to recognize the same diagnoses so both classifiers output corresponding probabilities for the same diagnosis and same patient based on different types of inputs. Each probability is a number representing the probability that a particular diagnosis exists based on the input report 410 and image 420, for example.

Verification unit 430 receives the probabilities from NLP classifier 411 and image classifier 421. Verification unit 430 may receive threshold pairs for each set of like probabilities from performance analysis unit 480, for example. When a probability output by each classifier 411 and 421 for the same diagnosis meets a particular threshold, the diagnosis is deemed to have been detected by the classifier based on the input data. Performance analysis unit 480 may generated one set of threshold pairs (th1A, th2A) having different values for probabilities generated by classifiers 411 and 421 for one diagnosis (e.g., lung nodules), and performance analysis unit 480 may generated another set of threshold pairs (th1B, th2B) having different values for probabilities generated by classifiers 411 and 421 for another diagnosis (e.g., liver nodules), for example. Each pair of thresholds may be generated based on analyzing training sets of manually generated data (e.g., doctor's reports) and corresponding machine generated data (e.g., DICOM images) for each particular diagnosis to generate optimum threshold pair values for each diagnosis to maximize the accuracy of one or more flags generated when image classifier 421 detects a particular diagnosis and NLP classifier 411 does not detect the same diagnosis. The one or more flags may be used to present information in a user interface to inform a user that a doctor's report may have missed a diagnosis, for example.

Figure 5:
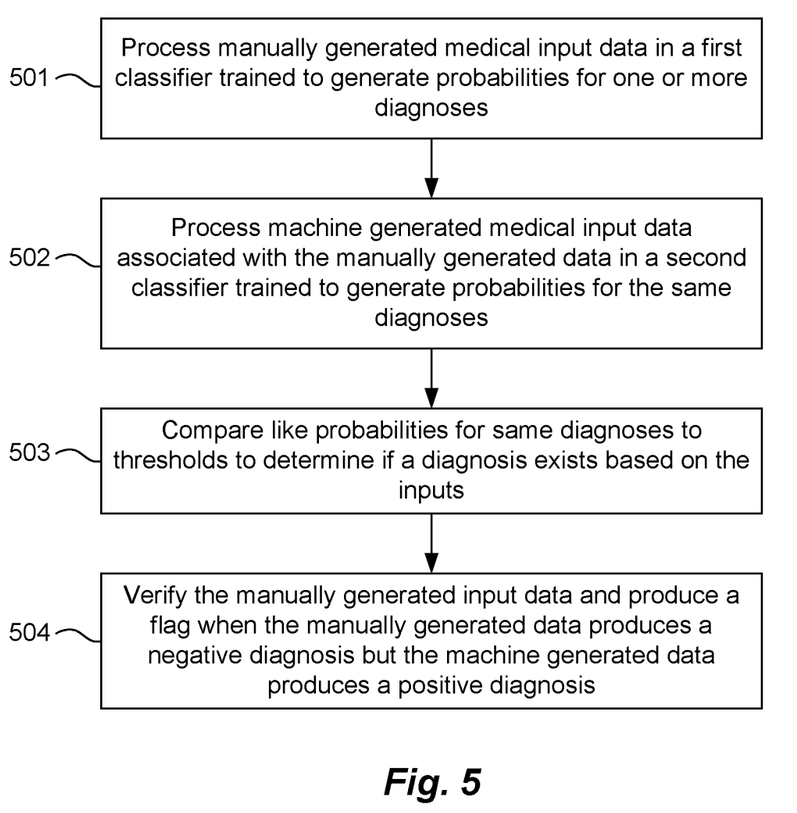
FIG. 5 illustrates a method of verifying a diagnosis according to one embodiment.

FIG. 5 illustrates a method of verifying a diagnosis according to one embodiment. At 501, manually generated medical input data is processed in a first classifier trained to generate probabilities for one or more diagnoses. At 502, machine generated medical input data associated with the manually generated data is processed in a second classifier trained to generate probabilities for the same diagnoses. At 503 like probabilities (e.g., probabilities for the same diagnosis) are compared to separate thresholds (e.g., threshold pairs for each diagnosis) to determine if a particular diagnosis is detected by each classifier based on of the manual/machine inputs. At 504, the manually generated input data is verified and a flag (e.g., a notification, message, or other software indicator) is generated when the manually generated input data produces a negative diagnosis but the machine generated input data produces a positive diagnosis.

Figure 6:
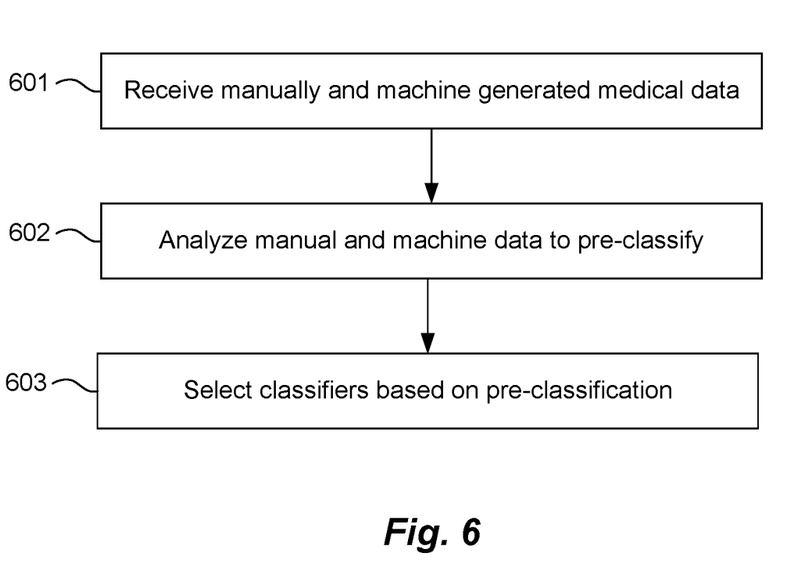
FIG. 6 illustrates a method of verifying a diagnosis according to another embodiment.

FIG. 6 illustrates a method of verifying a diagnosis according to another embodiment. At 601, manually generated medical data and associated machine generated medical data are received in supervisory pre-classification unit. At 602, the manual and machine generated data is analyzed to pre-classify each related pair of manual/machine data sets. At 603, classifiers may be selected based on the pre-classification to improve the accuracy of the system.

Figure 7:
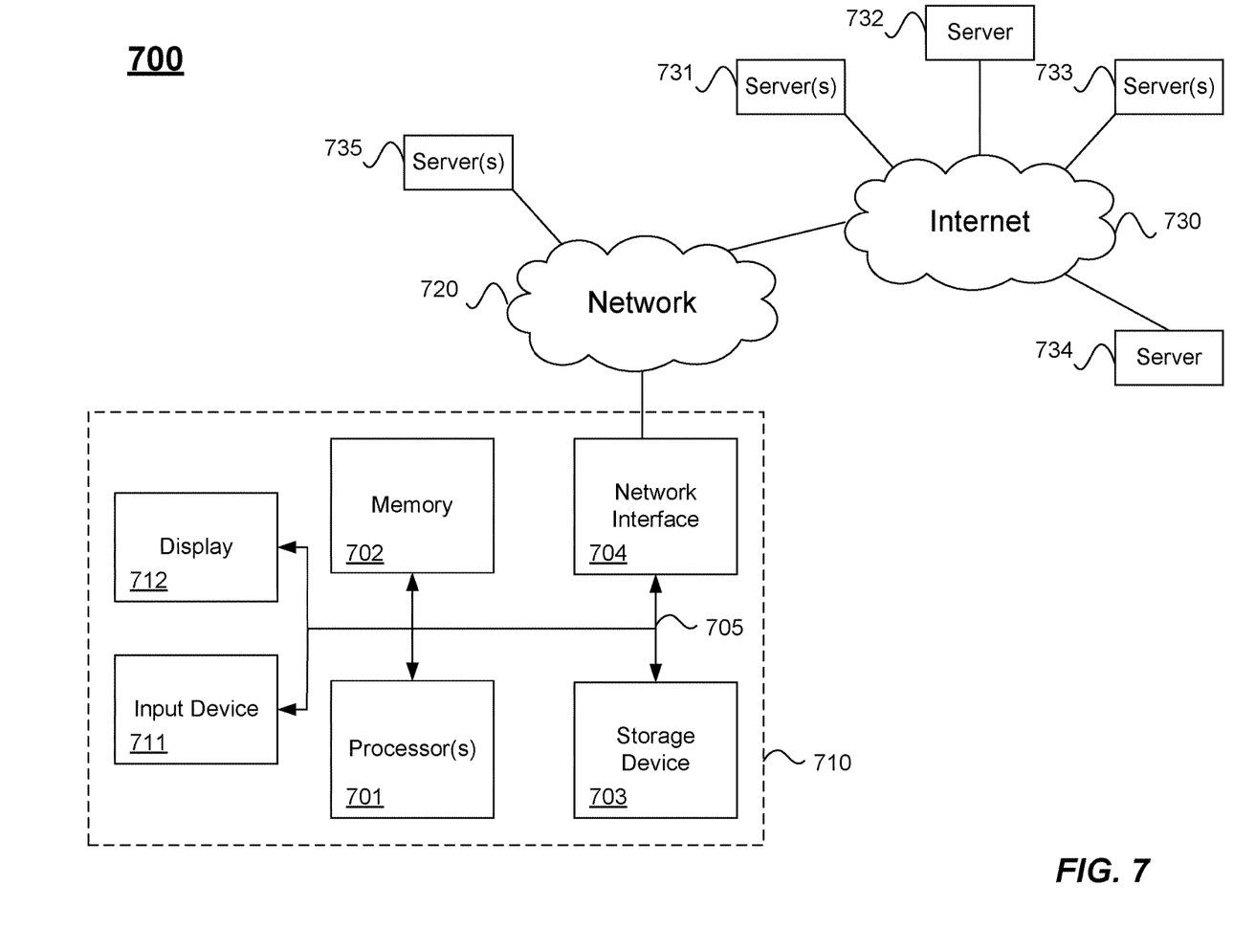
FIG. 7 illustrates computer hardware for executing software according to various embodiments.

FIG. 7 illustrates computer hardware for executing software according to various embodiments. The following hardware description is merely one illustrative example. It is to be understood that a variety of computers topologies may be used to implement the above described techniques. An example computer system 710 is illustrated in FIG. 7. Computer system 710 includes a bus 705 or other communication mechanism for communicating information, and one or more processor(s) 701 coupled with bus 705 for processing information. Computer system 710 also includes a memory 702 coupled to bus 705 for storing information and instructions to be executed by processor 701. Memory 702 may also be used for storing programs executed by processor(s) 701. Possible implementations of memory 702 may be, but are not limited to, random access memory (RAM), read only memory (ROM), or both. A storage device 703 is also provided for storing information and instructions. Common forms of storage devices include, for example, a hard drive, a magnetic disk, an optical disk, a CD-ROM, a DVD, a flash or other non-volatile memory, a USB memory card, or any other medium from which a computer can read. Storage device 703 may include source code, binary code, or software files for performing the techniques above, for example. Storage device 703 and memory 702 are both examples of non-transitory computer readable storage mediums.

Computer system 710 may be coupled via bus 705 to a display 712 for displaying information to a computer user. An input device 711 such as a keyboard, touchscreen, mouse and/or camera is coupled to bus 705 for communicating information and command selections from the user to processor 701 (e.g., in a software generated user interface). The combination of these components allows the user to communicate information with the system. In some systems, bus 705 represents multiple specialized buses for coupling various components of the computer together, for example.

Computer system 710 also includes a network interface 704 coupled with bus 705. Network interface 704 may provide two-way data communication between computer system 710 and a local network 720. Network 720 may represent one or multiple networking technologies, such as Ethernet, local wireless networks (e.g., WiFi), or cellular networks, for example. The network interface 704 may be a wireless or wired connection, for example. Computer system 710 can send and receive information through the network interface 704 across a wired or wireless local area network, an Intranet, or a cellular network to the Internet 730, for example. In some embodiments, a browser or local application, for example, may access data and features on back-end software systems that may reside on multiple different hardware servers on-prem 735 or across the Internet 730 on servers 731-734. One or more of servers 731-734 may also reside in a cloud computing environment, for example. Such servers may also comprise hardware such as memory, one or more processors, storage devices, buses, and a network interface, for example. In various embodiments, the above techniques may be implemented in an on-prem or cloud based server system, where machine generated and manually generate data is stored and the above techniques are performed on servers. The one or more flags mentioned above may be sent from a backend system on one or more servers to a local client on computer 710, for example, to notify a user of a discrepancy between a manually generated medical record and a related machine generated medical image, for example.

The above description illustrates various embodiments of the present disclosure along with examples of how aspects of the particular embodiments may be implemented. The above examples should not be deemed to be the only embodiments, and are presented to illustrate the flexibility and advantages of the particular embodiments as defined by the following claims. Based on the above disclosure and the following claims, other arrangements, embodiments, implementations and equivalents may be employed without departing from the scope of the present disclosure as defined by the claims.

What is claimed is:

1. A medical diagnostic system comprising:
a first classification unit trained to process manually generated medical input data, the first classification unit receiving first manually generated medical input data, and in accordance therewith, generating at least a first probability corresponding to at least a first medical diagnosis, wherein the first classification unit training comprises determining, based on a training data set, at least a first threshold configured to determine if the first probability from the first classification unit results in a first positive result for the first medical diagnosis;
a second classification unit trained to process machine generated medical input data, the second classification unit receiving first machine generated medical input data, and in accordance therewith, generating at least a second probability corresponding to at least the first medical diagnosis, wherein the second classification unit training comprises determining, based on the training data set, at least a second threshold configured to determine if the second probability from the second classification unit results in a second positive result for the first medical diagnosis; and
a verification unit configured to verify the manually generated input data by combining the first and second probabilities, wherein
the verification unit receives the first probability corresponding to the first medical diagnosis and the first threshold for determining if the first probability is high enough to result in the first positive result for the first medical diagnosis,
the verification unit receives the second probability corresponding to the first medical diagnosis and the second threshold for determining if the second probability is high enough to result in the second positive result for the first medical diagnosis, and
the verification unit compares the first probability to the first threshold to determine a positive or negative diagnosis and the verification unit compares the second probability to the second threshold to determine a positive or negative diagnosis.

2. The medical diagnostic system of claim 1 wherein the verification unit generates a verification flag when the second probability indicates a positive result for the first diagnosis, and the first probability indicates a negative result for the first diagnosis.

3. The medical diagnostic system of claim 1 wherein the manually generated medical input data and the machine generated medical input data correspond to the same patient, and wherein first manually generated medical input data for the patient is received and processed with first machine generated medical input data associated with the first manually generated medical input data.

4. The medical diagnostic system of claim 1 wherein the manually generated input data is verified when the first probability is greater than the first threshold and the second probability is greater than the second threshold, and the manually generated input data is verified when the first probability is less than the first threshold and the second probability is less than the second threshold.

5. A medical diagnostic method comprising:
determining, based on a training data set, at least a first threshold configured to determine if a first probability from a first classifier results in a first positive result for a first medical diagnosis;
determining, based on the training data set, at least a second threshold configured to determine if a second probability from a second classifier results in a second positive result for the first medical diagnosis;
processing, in the first classifier on one or more computers, manually generated medical input data, the first classifier trained to process the manually generated medical input data, the first classifier generating at least the first probability corresponding to at least the first medical diagnosis;
processing, in the second classifier on the one or more computers, machine generated medical input data, the second classifier trained to process the machine generated medical input data, the second classifier generating at least the second probability corresponding to at least the first medical diagnosis; and
verifying the manually generated input data by combining the first and second plurality of probabilities,
wherein verifying comprises:
receiving the first probability and the first threshold in a verification unit, the verification unit determining if the first probability is high enough to result in the first positive result for the first medical diagnosis,
receiving the second probability and the second threshold in the verification unit, the verification unit determining if the second probability is high enough to result in the second positive result for the first medical diagnosis,
wherein the verification unit compares the first probability to the first threshold to determine a positive or negative diagnosis and the verification unit compares the second probability to the second threshold to determine a positive or negative diagnosis.

6. The method of claim 5 further comprising generating a verification flag when the second probability indicates a positive result for the first diagnosis, and the first probability indicates a negative result for the first diagnosis.

7. The method of claim 5 further comprising:
pre-classifying the manually generated medical input data; and
selecting, based on the pre-classifying step, one of a plurality of classifiers, wherein the selected one of the plurality of classifiers is used as the first classifier.

8. The method of claim 5 further comprising:
pre-classifying the machine generated medical input data; and
selecting, based on the pre-classifying step, one of a plurality of classifiers, wherein the selected one of the plurality of classifiers is used as the second classifier.

9. The method of claim 5 wherein the manually generated medical input data is free-form text, text from a field in an electronic form, or text corresponding to a selection in an electronic form.

10. The method of claim 5 wherein the machine generated medical input data is an electronic image, electronic test results, or a video.

11. The method of claim 5 wherein the manually generated medical input data and the machine generated medical input data correspond to the same patient, and wherein first manually generated medical input data for the patient is received and processed with first machine generated medical input data associated with the first manually generated medical input data.

12. The method of claim 5 further comprising:
determining, from the manually generated medical input data, whether or not a first medical condition is present; and
selecting a first condition specific classifier for the first classifier and a first condition specific classifier for the second classifier when the condition is present, and selecting a second condition specific classifier for the first classifier and a second condition specific classifier for the second classifier when the condition is not present.

13. The method of claim 5 further comprising:
determining, based on the manually generated input data, a characteristic of a patient corresponding to the manually generated input data and machine generated input data; and
modifying the second classifier based on the characteristic of the patient.

14. The method of claim 13 wherein the characteristic of the patient is a gender of the patient.

15. The method of claim 13 wherein the characteristic of the patient is an age of the patient.

16. The method of claim 5, wherein the machine generated input data is an image, the method further comprising:
determining a scan quality of the image; and
selecting the second classifier from a plurality of classifiers based on the scan quality.

17. The method of claim 5, wherein the machine generated input data has associated metadata specifying a scan type, the method further comprising:
determining a scan type from the metadata; and
selecting the second classifier from a plurality of classifiers based on the scan type specified in the metadata.

18. The method of claim 17, further comprising selecting the first classifier from a plurality of classifiers based on the scan type specified in the metadata.

19. The method of claim 5 wherein the training data set comprises manually generated medical input data and machine generated input data corresponding to at least the first medical diagnosis.

20. The method of claim 5 wherein probabilities for a particular diagnosis are analyzed across the training data set to generate the thresholds pairs.

21. A non-transitory machine-readable medium storing a program executable by at least one processing unit of a computer, the program comprising sets of instructions for:
determining, based on a training data set, at least a first threshold configured to determine if a first probability from a first classifier results in a first positive result for a first medical diagnosis;
determining, based on the training data set, at least a second threshold configured to determine if a second probability from a second classifier results in a second positive result for the first medical diagnosis;
processing, in the first classifier on one or more computers, manually generated medical input data, the first classifier trained to process the manually generated medical input data, the first classifier generating at least the first probability corresponding to at least the first medical diagnosis;
processing, in the second classifier on the one or more computers, machine generated medical input data, the second classifier trained to process the machine generated medical input data, the second classifier generating at least the second probability corresponding to at least the first medical diagnosis; and
verifying the manually generated input data by combining the first and second plurality of probabilities,
wherein verifying comprises:
receiving the first probability and the first threshold in a verification unit, the verification unit determining if the first probability is high enough to result in the first positive result for the first medical diagnosis,
receiving the second probability and the second threshold in the verification unit, the verification unit determining if the second probability is high enough to result in the second positive result for the first medical diagnosis,
wherein the verification unit compares the first probability to the first threshold to determine a positive or negative diagnosis and the verification unit compares the second probability to the second threshold to determine a positive or negative diagnosis.

* * * * *